United States Patent
Molz, IV et al.

(10) Patent No.: US 7,811,328 B2
(45) Date of Patent: Oct. 12, 2010

(54) SYSTEM, DEVICE AND METHODS FOR REPLACING THE INTERVERTEBRAL DISC WITH A MAGNETIC OR ELECTROMAGNETIC PROSTHESIS

(75) Inventors: Fred J. Molz, IV, Collierville, TN (US); Thomas Carls, Memphis, TN (US); Aurelien Bruneau, Memphis, TN (US); Eric C. Lange, Collierville, TN (US); Matthew M. Morrison, Cordova, TN (US); Jonathan Dewey, Memphis, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1162 days.

(21) Appl. No.: 11/118,277

(22) Filed: Apr. 29, 2005

(65) Prior Publication Data

US 2006/0247782 A1    Nov. 2, 2006

(51) Int. Cl.
*A61F 2/44* (2006.01)
(52) U.S. Cl. .................................. 623/17.16
(58) Field of Classification Search ... 623/17.11–17.16, 623/18.12; 606/61, 66, 86, 88; 600/12
See application file for complete search history.

(56) References Cited

U.S. PATENT DOCUMENTS

| | | | | |
|---|---|---|---|---|
| 2,662,228 A * | 12/1953 | Bennington | ................ | 623/24 |
| 4,024,588 A * | 5/1977 | Janssen et al. | ........... | 623/18.12 |
| 5,236,460 A * | 8/1993 | Barber | ................ | 623/17.15 |
| 5,258,031 A * | 11/1993 | Salib et al. | ................ | 623/17.15 |
| 5,507,835 A * | 4/1996 | Jore | ................ | 623/36 |
| 5,595,563 A * | 1/1997 | Moisdon | ................ | 600/12 |
| 5,879,386 A * | 3/1999 | Jore | ................ | 623/16.11 |
| 6,110,210 A | 8/2000 | Norton et al. | | |
| 6,292,680 B1 * | 9/2001 | Somogyi et al. | ........... | 600/407 |
| 6,599,321 B2 * | 7/2003 | Hyde, Jr. | ................ | 623/18.12 |
| 6,645,248 B2 * | 11/2003 | Casutt | ................ | 623/17.12 |
| 6,899,667 B2 * | 5/2005 | Becker et al. | ................ | 600/9 |
| 2002/0032484 A1 * | 3/2002 | Hyde, Jr. | ................ | 623/18.12 |
| 2003/0014111 A1 * | 1/2003 | Ralph et al. | ................ | 623/17.13 |
| 2003/0187510 A1 * | 10/2003 | Hyde | ................ | 623/18.12 |
| 2003/0236572 A1 * | 12/2003 | Bertram, III | ................ | 623/18.12 |
| 2004/0059423 A1 * | 3/2004 | Barnes et al. | ................ | 623/18.12 |
| 2004/0260396 A1 | 12/2004 | Ferree et al. | | |
| 2005/0027364 A1 * | 2/2005 | Kim et al. | ................ | 623/17.13 |
| 2005/0234555 A1 * | 10/2005 | Sutton et al. | ................ | 623/17.15 |
| 2006/0069447 A1 * | 3/2006 | DiSilvestro et al. | ...... | 623/23.16 |
| 2006/0079897 A1 * | 4/2006 | Harrison et al. | ................ | 606/61 |

FOREIGN PATENT DOCUMENTS

DE    2821 678 A1    11/1979

\* cited by examiner

*Primary Examiner*—Thomas C Barrett
*Assistant Examiner*—Nicholas Woodall

(57) ABSTRACT

One embodiment of the present application includes a spinal disk prosthesis with one end portion to form a load transmitting relationship with one vertebra of a patient's spine and another end portion to form a load transmitting relationship with another vertebra of the patient's spine. A tube connects the end portions together and a damping material is positioned inside the tube. The end portions each include a magnet to generate a corresponding magnetic field. These magnetic fields are oriented to provide a repulsive force between the end portions to provide a magnetic bearing.

20 Claims, 3 Drawing Sheets

SYSTEM, DEVICE AND METHODS FOR REPLACING THE INTERVERTEBRAL DISC WITH A MAGNETIC OR ELECTROMAGNETIC PROSTHESIS

BACKGROUND

The present invention relates to a prosthetic device and manner of using the same, and more particularly, but not exclusively, relates to a prosthesis that provides a magnetic load bearing and is configured for implantation between bones of a patient. Optionally, this bearing may be made to dynamically operate and/or adjust to different applications.

The use of prosthetic implants to address orthopedic injuries and ailments has become commonplace. Nonetheless, further challenges exist in regard to various manufacturing and operational aspects of such devices. Thus, there is a need for additional contributions in this area of technology.

SUMMARY

One embodiment of the present application is a unique prosthesis. Other embodiments include unique methods, systems, devices, and apparatus involving an implantable prosthesis.

A further embodiment includes a unique load bearing prosthesis. That is arranged for implantation in a space formed between two or more bones and provides a magnetic bearing for mechanical loads imparted by one or more of these bones.

Another embodiment includes: forming a cavity between two vertebrae of a patient's spine; implanting a spinal disk prostheses in the cavity that includes opposing end portions to engage each of the vertebrae and a prosthetic linking structure that connects the end portions together. Also, a magnetic field is provided with each of the end portions to provide a repulsive magnetic force to maintain the end portions in a spaced apart relationship while engaged in a load bearing relationship with the vertebrae. In one form, the magnetic field of at least one of the end portions is provided with an electromagnet, and in another form at least one of the end portions is provided with a permanent magnet. Alternatively or additionally, the prosthetic structure includes a sleeve containing a damping material placed between the end portions.

Still another embodiment is directed to a spinal disk prosthetic device for implantation in an intervertebral cavity. This device includes a first end portion to engage a first one of the vertebrae, a second end portion to engage a second one of the vertebrae that is positioned opposite the first end portion. The first end portion is structured to provide a first magnetic pole and the second end portion is structured to provide a second magnetic pole, with both the poles being of the same type. A coupling structure connects the first end portion and the second end portion together to direct the first pole and the second pole toward one another and generate a repulsive magnetic force to maintain the first end portion and the second end portion in a spaced apart relationship when bearing a load.

Yet a further embodiment, includes: performing surgery to form an cavity between two or more bones of a patient; implanting a prostheses in the cavity to establish a load bearing relationship between the bones, that includes a first load bearing member opposite a second load bearing member and a linking structure connecting the first member and the second member together; and providing a magnetic field pattern between the first member and the second member. This pattern is oriented to generate a repulsive magnetic force that maintains the first member and the second member in a spaced apart relationship while engaged in a load bearing relationship between the bones.

Still a further embodiment is directed to a system comprising a prosthesis and a magnetic field controller. The prosthesis includes a first load bearing portion opposite a second load bearing portion and a coupling structure connecting these portions together. The magnetic field controller is in communication with the prosthesis to adjust generation of a magnetic field pattern provided with the portions. This pattern is configured to generate a repulsive magnetic force between the load bearing portions to maintain them in a spaced apart relationship when the prosthesis is implanted between two or more bones.

One object of the present application is to provide a unique prosthesis.

Alternatively or additionally, another object of the present application is to provide a unique prosthesis method, system, device, or apparatus.

Further embodiments, forms, features, aspects, benefits, objects, and advantages of the present application shall become apparent from the detailed description and figures provided herewith.

DETAILED DESCRIPTION OF SELECTED EMBODIMENTS

Figure 1:
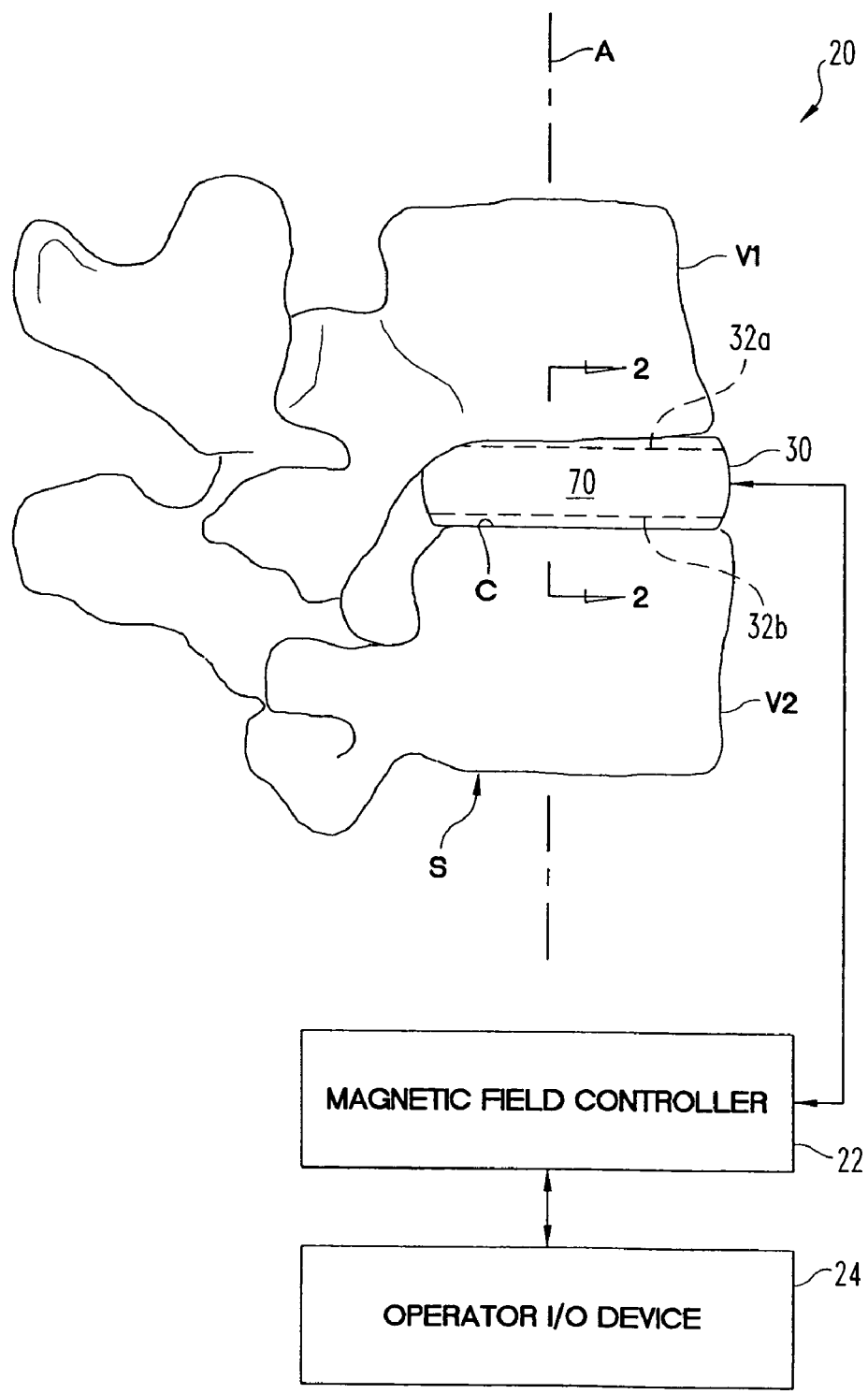
FIG. 1 is a partial diagrammatic view of a system including a prosthesis with a magnetic bearing.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present application is a prosthesis arranged for implantation between two or more bones inside a patient's body. The prosthesis includes opposing magnetic field generating portions that are oriented to provide a repulsive magnetic force there between, that is used for load bearing. In one form, the magnetic field pattern resulting from the magnetic field generating portions is adjustable to accommodate different levels of physical activity of a given patient and/or to customize operation of the prosthesis to a given patient.

FIG. 1 depicts prosthesis system 20 of a further embodiment of the present application. System 20 is partially diagrammatic and is shown in relation to a portion of spine S of a patient along axis A. Axis A is the nominal load bearing axis for spine S when the patient's upper body is upright. Spine S is shown with representative vertebra V1 and vertebra V2. System 20 includes magnetic field controller 22 in operational communication with operator Input/Output (I/O) device 24 and spinal disk prosthesis 30. Prosthesis 30 is positioned between vertebra V1 and vertebra V2 in intervertebral cavity C and is configured to provide a magnetic bearing 70 as further described hereinafter. The intervertebral space between vertebrae V1 and V2 (cavity C) is typically formed by removing a diseased and/or injured spinal disk during surgery. Prosthesis 30 is then implanted in cavity C in a subsequent stage of this surgical procedure.

Figure 2:
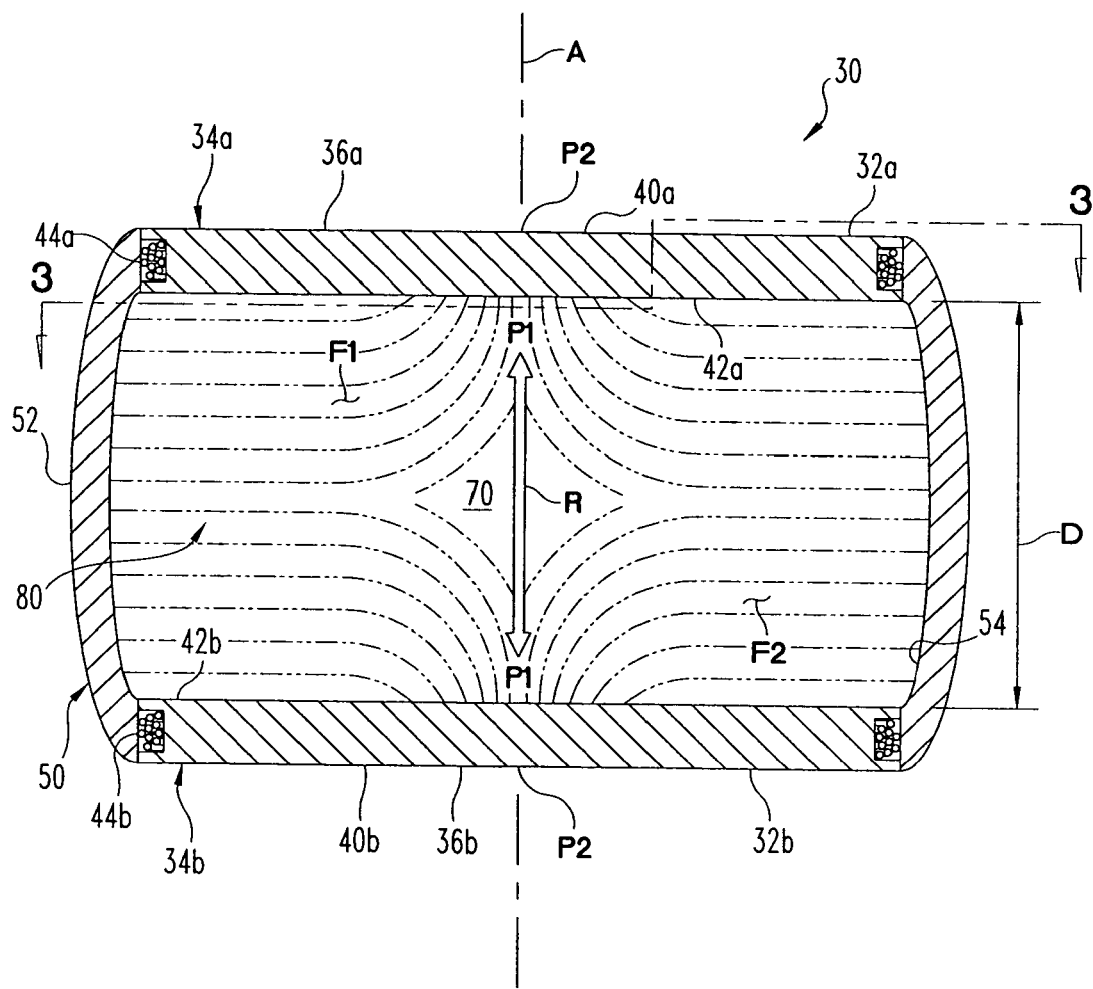
FIG. 2 is a cross sectional side view of the FIG. 1 prosthesis taken along section line 2-2 shown in FIG. 1.
Figure 3:
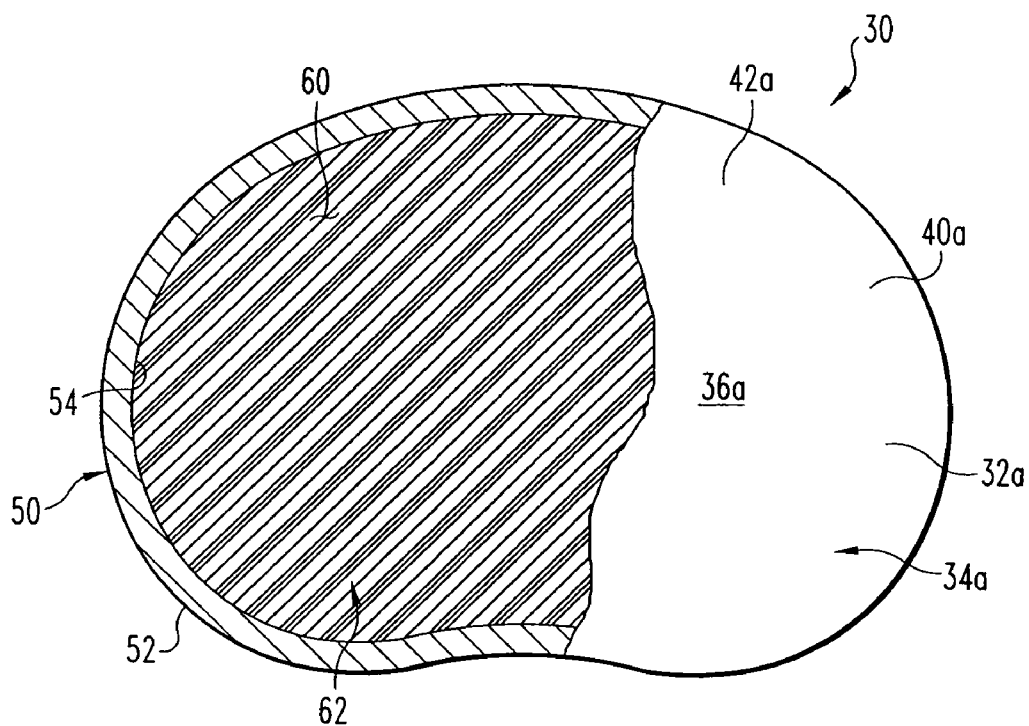
FIG. 3 is a partial sectional, cutaway view of the FIG. 1 prosthesis taken along the section line 3-3 shown in FIG. 2.

Referring additionally to FIGS. 2 and 3, further details concerning prosthesis 30 are shown. FIG. 2 is a cross sectional view corresponding to section line 2-2 shown in FIG. 1, and FIG. 3 is a partial sectional, cutaway view corresponding to section line 3-3 shown in FIG. 2. Prosthesis 30 includes end portion 32a opposite end portion 32b. End portion 32a includes load bearing member 34a defining bearing surface 36a that is structured to be placed against vertebra V1 in a mechanical load transmitting or bearing relationship. End portion 32b includes load bearing member 34b defining bearing surface 36b that is structured to be placed against vertebra V2 in a mechanical load transmitting or bearing relationship.

End portions 32a and 32b each include a respective one of magnets 40a and 40b. For prosthesis 30, magnets 40a and 40b are further designated as corresponding electromagnets 42a and 42b. Electromagnets 42a and 42b each have a corresponding electrically conductive coil 44a and 44b of a standard type, which are schematically shown in section. Prosthetic linking structure 50 interconnects end portions 32a and 32b. This interconnection can be by an adhesive, one or more fasteners, or such other joining technique as would occur to those skilled in the art. As illustrated, linking structure 50 is in the form of a flexible fabric sleeve or tube 52. Tube 52 can be formed of woven natural fibers and/or synthetic fibers, and can be readily reshaped and reformed by hand. Examples of materials comprising the fabric of the tube 52 include glass, graphite, metal, and/or an organic polymer. Tube 52 defines chamber 54 between end portions 32a and 32b. Damping material 60 is positioned in chamber 54, and is more specifically shown as a resilient polymeric solid 62. In one form, solid 62 is in the form of one or more types of silicone. It should be appreciated that damping material 60 is not shown in section in FIG. 2 to preserve clarity, but would appear similar to damping material 60 shown in FIG. 4, which is further described hereinafter.

Referring generally to FIGS. 1-3, certain operational aspects of system 20 are next described. When it becomes necessary to replace a natural spinal disk due to disease, injury, congenital defect, or the like; surgical intervention may be indicated. In one surgical procedure, the defective disk is removed from between adjacent vertebrae, the resulting intervertebral space (cavity C) is cleared and prepared, and prosthesis 30 is implanted into cavity C. In so doing, load bearing member 34a is arranged to be placed against one vertebra (vertebra V1 in FIG. 1) and load bearing member 34b is arranged to be placed against an opposing vertebra (vertebra V2 in FIG. 1).

It should be appreciated that during a significant portion of its nominal use after implantation, prosthesis 30 will be compressively loaded, such as when the patient is upright. To mechanically counteract this compressive loading, magnetic bearing 70 is provided by prosthesis 30, and is configured to maintain a desired nominal degree of spacing between members 34a and 34b while within spine S. For system 20, magnetic bearing 70 is activated and controlled by magnetic field controller 24. Controller 24 is responsive to operator input with device 22 to selectively activate and/or adjust electromagnets 42a and 42b. Electromagnets 42a and 42b are oriented with like magnetic poles P1 being directed inwardly toward one another in an opposing relationship. Correspondingly, the opposite poles P2 of each electromagnet are outwardly directed. It should be appreciated that pole P1 can be of a North (N) or South (S) type with pole P2 being of the other (opposite) type for each magnet 40a and 40b.

For this orientation with like poles opposing each other, activated electromagnets 42a and 42b, and correspondingly end portions 32a and 32b, repel one another with repulsive magnetic force R as represented by a double-headed arrow in FIG. 2. The corresponding magnetic fields F1 and F2 of electromagnets 42a and 42b are represented by partially depicted broken field lines inside chamber 54. As represented by these field lines, fields F1 and F2 repel one another in a standard manner expected for like magnetic poles. Field lines outside chamber 54 have been omitted to preserve clarity. Collectively, magnetic fields F1 and F2 provide a magnetic field pattern 80 that corresponds to the repulsive magnetic force that is used to bear compressive loading by spine S.

The repulsive magnetic force R causes end portions 32a and 32b to remain spaced apart from one another a maximum distance D as defined by linking structure 50. In particular, for the illustrated fabric tube 52 that is readily reshaped by hand, the repulsive magnetic force R places linking structure 50 under tension when no counteracting force is applied. Consequently, linking structure 50 maintains the polar orientation of magnets 40a and 40b and correspondingly constrains end portions 32a and 32b to maximum distance D. Furthermore, when in use, prosthesis 30 is subjected to loads along axis A through vertebra V1 and/or V2, and is operable to transmit loading from one to the other along axis A. However, because force R is finite, it can be offset to some extent by this external loading, with the tendency for end portions 32a and 32b to move closer to one another along axis A in response. Further, with this relative motion between end portions 32a and 32b, damping material 60 tends to be compressed and for its particular form as solid 62, it bulges outward slightly as illustrated in FIG. 2. Correspondingly, damping material 60 cushions the axial compressive load, complimenting magnetic bearing 70—particularly with respect to sudden changes in load. Collectively, tube 52 and solid 62 also limit movement along a direction orthogonal to axis A, resisting shear loads that could dislocate member 34a and/or member 34b relative to axis A.

Several system control modes are contemplated. In one example, magnetic field controller 22 remains outside the patient's body, and is only used during or soon after implantation of prosthesis 30 to adjust the magnetic field pattern 80 to a desired load-bearing level, using device 24 to provide adjustment input. For this mode, controller 22 can be external or internal and can be used to set the output of an implanted electric power source (not shown) for electromagnets 42a and 42b that corresponds to the selected load-bearing level. Once the level is set, controller 22 is no longer needed, and can be removed, such that the magnetic field pattern 80 is maintained by this implanted power source. In another mode, controller 22 may be periodically activated by a physician or other health care provider to "fine tune" or otherwise adjust the operation of prosthesis 30. For this mode, controller 22 may be implanted with or without device 24, and may include an implanted electric power source for electromagnets 42a and 42b; controller 22, and/or device 24 as needed. In still another mode, controller 22, and optionally device 24 are implanted with the patient (user) being able to selectively adjust the magnetic field pattern in accordance with anticipated physical activities or the like. An electric power supply for electromagnets 42a and 42b, controller 22, and/or device 24 can likewise be implanted for this mode.

Alternatively or additionally, another mode provides for the reduction or elimination of the magnetic field so that it does not interfere or disrupt other fields for safety reasons or otherwise. For such a mode, the nonmagnetic components are mechanically configured to provide a desired load support structure when the magnetic field is reduced or absent. This mechanical structure can be aimed at temporary usage or longer term usage as appropriate. In still other embodiments, different control or regulation modes are contemplated as would occur to one skilled in the art. In one alternative in particular, there is no adjustment capability for the magnetic field at all, and/or controller 22 and device 234 are absent.

Figure 4:
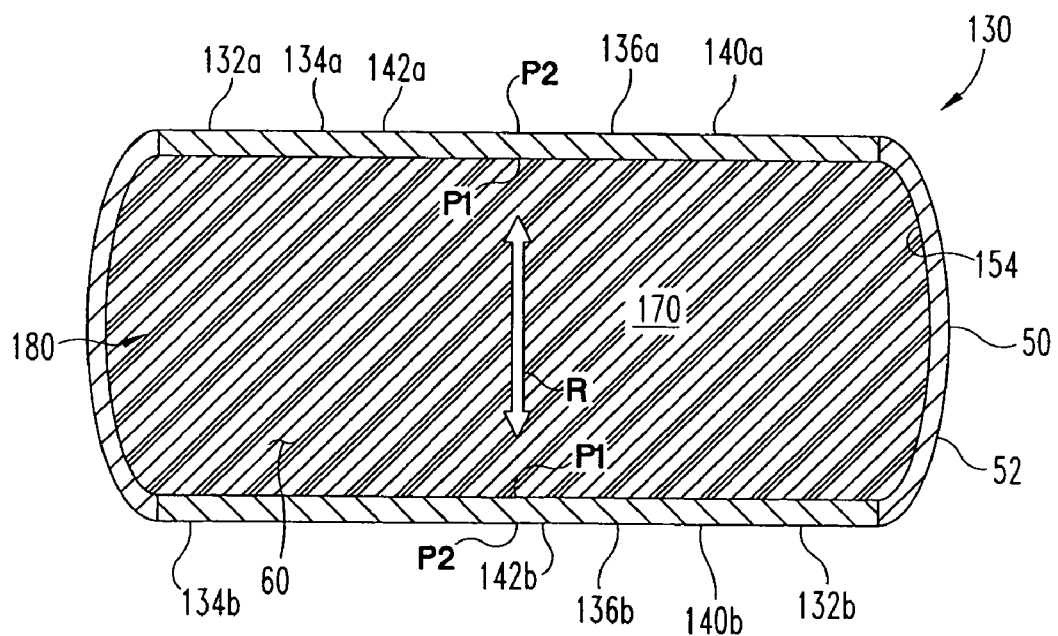
FIG. 4 is a partial diagrammatic, partial cross sectional side view of another type of prosthesis with a magnetic bearing.

Referring to FIG. 4, an alternative embodiment is illustrated as spinal disk prosthesis 130; where like reference numerals refer to like features. Prosthesis 130 is arranged to be implanted in an intervertebral space to bear against vertebrae the same as prosthesis 30. Like prosthesis 30, prosthesis 130 includes opposing end portions 132a and 132b that each include a respective load bearing member 134a and 134b. Load bearing members 134a and 134b define respective load bearing surfaces 136a and 136b. End portions 132a and 132b are also interconnected by linking structure 50 in the form of fabric tube 52, which defines chamber 154. Tube 52 encloses damping material 60 inside chamber 154, as previously described in connection with system 20.

End portions 132a and 132b each include a corresponding magnet 140a and 140b. In contrast to magnets 40a and 40b, magnets 140a and 140b are each of a permanent magnet type as further designated by reference numerals 142a and 142b, respectively. Permanent magnets 142a and 142b are oriented with like poles P1 being directed inward toward one another to create a repulsive magnetic force R as described in connection with prosthesis 30. Correspondingly, poles P2 (each opposite pole P1) are outwardly directed away from one another. Similar to prosthesis 30, the orientation of poles P1 provides magnetic bearing 170 that may be used in a comparable manner. Likewise, magnetic field pattern 180 results from this polar orientation.

Like prosthesis 30, prosthesis 130 can be made so that magnetic field pattern 180 and resulting force R are adjustable. With permanent magnets, such adjustments can be made mechanically by orienting various permanent magnet polar geometries and corresponding shapes relative to one another. U.S. Pat. No. 5,595,563 to Moisdon describes further background regarding such adjustment techniques, which is hereby incorporated by reference in its entirety. Alternatively or additionally, electromagnets could be used in combination with permanent magnets to provide adjustability.

Several other embodiments of the present invention are envisioned. For example, one alternative combines various aspects of system 20 and prosthesis 130. In yet another embodiment, prosthesis 30, prosthesis 130, or a variant thereof is implanted between two or more bones other than vertebrae.

In further embodiments, the magnets and corresponding fields and the resultant magnetic field pattern can include both attraction forces from placement of opposite pole types in proximity to one another and repulsion forces from placement of like pole types in proximity to one another. As used herein, "repulsive magnetic force" or "repulsive force" refers to a force resulting from the placement of like magnetic poles in proximity to one another either with or without attractive forces also being present due to opposite magnetic poles being placed in proximity to one another, and further refers to any one of such forces when multiple instances are present. U.S. Pat. No. 6,387,096 is cited as a source of additional information concerning repulsive forces that are provided together with attractive magnetic forces, which is hereby incorporated by reference. In another alternative embodiment example, one or more of surfaces 36a, 36b, 136a, and 136b are roughened or otherwise include bone-engaging structures to secure purchase with vertebral surfaces.

In yet other embodiments, the prosthetic linking structure can include one or more tethers, cables, braids, wires, cords, bands, filaments, fibers, and/or sheets; a nonfabric tube comprised of an organic polymer, metal, and/or composite; an accordion or bellows tube type that may or may not include a fabric, filamentous, fibrous, and/or woven structure; a combination of these, or such different arrangement as would occur to one skilled in the art. Alternatively or additionally, the linking structure can be arranged to present one or more openings between linking structure members or portions, where such openings extend between end portions of the prosthesis. In one particular alternative, a number of spaced apart cords connect opposing end portions and define relatively large open spaces lateral to axis A. In still other embodiments, damping material 60 can be in the form of a fluid contained in a fluid-tight chamber defined by the linking structure between the opposing end portions and/or can be comprised of a solid other than silicone. For such fluid-based arrangements, the linking structure is of a type suitable to retain the fluid, such as a flexible or elastic organic polymer tube structure or a metallic bellows or accordion tube structure.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method, comprising:
    forming a cavity between a first vertebra and a second vertebra of a patient's spine;
    implanting a spinal disk prosthesis in the cavity, the prosthesis including a first end portion to engage the first vertebra and a second end portion to engage the second vertebra, the first end portion and the second end portion being connected together by a prosthetic linking structure and wherein the first end portion includes a first electrically conductive coil, and wherein the second end portion includes a second electrically conductive coil; and
    providing a first magnetic field with the first electrically conductive coil of the first end portion and a second magnetic field with the second electrically conductive coil of the second end portion, and wherein the first magnetic field and the second magnetic field are configured to provide a repulsive magnetic force to maintain the first end portion and the second end portion in a spaced apart relationship while engaged in a load bearing relationship with the first vertebra and the second vertebra; and electrically adjusting at least one of the first magnetic field and the second magnetic field with an electronic magnetic field controller in operative communication with the first electrically conductive coil and the second electrically conductive coil of the spinal disk prosthesis, the electrically adjusting occurring after the implanting of the spinal disk prosthesis when the spinal disk prosthesis is implanted between the first vertebra and the second vertebra with the spinal disk prosthesis maintained in the cavity to adjust the repulsive magnetic force between the first and second portions to a desired load bearing level;

determining a level of patient physical activity relative to the prosthesis; and changing at least one of the first magnetic field and the second magnetic field in response to the level of patient physical activity.

2. An apparatus, comprising:

a spinal disk prosthetic device for implantation in an intervertebral cavity, the prosthetic device including:

a first end portion to engage a first one of the vertebrae, the first end portion including a first magnet having a first electrically conductive coil disposed about the periphery of the first end portion to provide a first magnetic pole;

a second end portion to engage a second one of the vertebrae and being positioned opposite the first end portion, the second end portion including a second magnet having a second electrically conductive coil disposed about the periphery of the second end portion to provide a second magnetic pole; and a linking structure connected to the first end portion and the second end portion to position the first magnet and the second magnet with like magnetic poles oriented in direct opposition to one another in an opposing relationship along a load bearing axis to generate a repulsive magnetic force therebetween, wherein the like poles of the first and second magnets generate magnetic fields that directly oppose one another along the load bearing axis with the repulsive magnetic force acting along the load bearing axis, the linking structure constraining separation of the first end portion and the second end portion in response to the repulsive magnetic force to a maximum distance and permitting relative movement between the first end portion and the second end portion in response to variation of a compressive load transmitted from one or more of the vertebrae.

3. The apparatus of claim 2, wherein the linking structure includes one or more of a braid, woven fabric, natural fiber, organic polymer, and metallic filament.

4. The apparatus of claim 2, wherein at least one of the first magnet and the second magnet comprises an electromagnet.

5. The apparatus of claim 2, further comprising means for selectively adjusting the repulsive magnetic force between the first and second load bearing members to a desired load bearing level after the spinal disk prosthetic device is implanted into the intervertebral cavity, said means for selectively adjusting operating to adjust the repulsive magnetic force when the spinal disk prosthetic is implanted between the first and second vertebrae with the spinal disk prosthesis maintained in the intervertebral cavity.

6. An apparatus, comprising:

a spinal disk prosthetic device for implantation in an intervertebral cavity, the prosthetic device including:

a first end portion to engage a first one of the vertebrae, the first end portion including a first electrically conductive coil to provide a first magnetic pole;

a second end portion to engage a second one of the vertebrae and being positioned opposite the first end portion, the second end portion including a second electrically conductive coil; and a linking structure connected to the first end portion and the second end portion to position the first electrically conductive coil and the second electrically conductive coil with like poles directed toward one another to generate a repulsive magnetic force therebetween, the linking structure constraining separation of the first end portion and the second end portion in response to the repulsive magnetic force to a maximum distance and permitting relative movement between the first end portion and the second end portion in response to variation of a compressive load transmitted from one or more of the vertebrae; and a magnetic field controller in operative communication with the first electrically conductive coil and the second electrically conductive coil to control a magnetic field generated therewith after implantation of the spinal disk prosthetic device within the intervertebral cavity when the spinal disk prosthetic device is implanted between the first and the second vertebrae with the spinal disk prosthetic device maintained in the intervertebral cavity to adjust the repulsive magnetic force between the first and second end portions to a desired load bearing level.

7. A method, comprising:

selecting a prosthesis including a first load bearing member opposite a second load bearing member and a linking structure connected to the first load bearing member and the second load bearing member;

implanting the prosthesis in a cavity between two or more bones of a patient by positioning the first load bearing member against a first one of the bones and the second load bearing member against a second one of the bones to establish a load bearing relationship between the bones; and providing a magnetic field pattern between the first load bearing member and the second load bearing member using a first electrically conductive coil disposed at the first load bearing member and a second electrically conductive coil disposed at the second load bearing member, the magnetic field pattern being oriented to generate a repulsive magnetic force to maintain the first load bearing member and the second load bearing member in a spaced apart relationship while engaged in a compressive load bearing relationship between the bones; and selectively adjusting the magnetic field pattern after the implanting of the prosthesis in the cavity to adjust the repulsive magnetic force between the first and second load bearing members to a desired load bearing level.

8. The method of claim 7, wherein said providing is performed with a first electromagnet carried with the first load bearing member.

9. The method of claim 7, wherein the linking structure includes one or more of a fibrous, filamentous, organic polymer, woven, braid, cord, wire, band, and fabric material.

10. The method of claim 7, wherein the linking structure includes a fabric sleeve enclosing a damping material positioned between the first load bearing member and the second load bearing member, and further comprising providing for removal of the magnetic field pattern, the fabric sleeve and the damping material being structured to mechanically provide load support in the absence of the repulsive magnetic force.

11. The method of claim 7, wherein the selectively adjusting of the magnetic field pattern occurs when the prosthesis is implanted between the bones with the prosthesis maintained in the cavity between the bones to adjust the repulsive magnetic force between the first and second load bearing members to the desired load bearing level.

12. A method, comprising:
selecting a prosthesis including a first load bearing member having a first electrically conductive coil opposite a second load bearing member having a second electrically conductive coil and a linking structure connected to the first load bearing member and the second load bearing member;
implanting the prostheses in a cavity between two or more bones of a patient by positioning the first load bearing member against a first one of the bones and the second load bearing member against a second one of the bones to establish a load bearing relationship between the bones; and
providing a magnetic field pattern between the first load bearing member and the second load bearing member, the magnetic field pattern being oriented to generate a repulsive magnetic force to maintain the first load bearing member and the second load bearing member in a spaced apart relationship while engaged in a compressive load bearing relationship between the bones; and
electrically adjusting the magnetic field pattern with an electronic magnetic field controller in operative communication with the first and second electrically conductive coils of the prosthesis in response to an operator input, the electrically adjusting occurring after the implanting of the prosthesis when the prosthesis is implanted between the first vertebra and the second vertebra with the spinal disk prosthesis maintained in the cavity to adjust the repulsive magnetic force between the first and second portions to a desired load bearing level.

13. A spinal disk prosthesis:
a first end portion to form a load transmitting relationship with a first vertebra of a patient's spine;
a second end portion to form a load transmitting relationship with a second vertebra of the patient's spine, the second end portion being positioned opposite the first end portion;
a sleeve connecting the first end portion and the second end portion together;
a damping material positioned inside the sleeve between the first end portion and the second end portion; and
wherein the first end portion includes a first magnet having a first electrically conductive coil disposed about the periphery of the first end portion to generate a first magnetic field and the second end portion includes a second magnet having a second electrically conductive coil disposed about the periphery of the second end portion to generate a second magnetic field, the first magnet and the second magnet including like magnetic poles oriented in direct opposition to one another in an opposing relationship along a load bearing axis such that the first magnetic field and the second magnetic field directly oppose one another along the load bearing axis to provide a repulsive magnetic force between the first end portion and the second end portion when the first magnetic field and the second magnetic field are generated therewith.

14. The prosthesis of claim 13, wherein the first magnetic structure includes a first electromagnet and the second magnetic structure includes a second electromagnet, and the first electromagnet and the second electromagnet are operable to generate the like magnetic poles that are inwardly directed toward one another to provide the repulsive magnetic force.

15. The prosthesis of claim 13, further comprising means for selectively adjusting the repulsive magnetic force between the first end portion and the second end portion to a desired load bearing level after the spinal disk prosthesis is implanted into an intervertebral cavity between the first and second vertebrae, said means for selectively adjusting operating to adjust the repulsive magnetic force when the spinal disk prosthetic is implanted between the first and second vertebrae with the spinal disk prosthesis maintained in the intervertebral cavity.

16. A method, comprising:
forming a cavity between a first vertebra and a second vertebra of a patient's spine;
implanting a spinal disk prosthesis in the cavity, the prosthesis including a first end portion to engage the first vertebra and a second end portion to engage the second vertebra, the first portion and the second portion being connected together by a prosthetic linking structure; and
providing a first magnetic field using a first electrically conductive coil disposed at the first portion and a second magnetic field using a second electrically conductive coil disposed at the second portion, the first magnetic field and the second magnetic field being configured to provide a repulsive magnetic force to maintain the first portion and the second portion in a spaced apart relationship while engaged in a load bearing relationship with the first vertebra and the second vertebra; and
selectively adjusting at least one of the first magnetic field and the second magnetic field after the implanting of the spinal disk prosthesis in the cavity to adjust the repulsive magnetic force between the first and second portions to a desired load bearing level;
wherein the first and second magnetic fields are provided by the first and second electrically conductive coils including like magnetic poles oriented in direct opposition to one another in an opposing relationship along a load bearing axis such that the first magnetic field and the second magnetic field directly oppose one another along the load bearing axis with the repulsive magnetic force acting along the load bearing axis.

17. The method of claim 16, wherein the first end portion includes an electromagnet and said providing is performed with the electromagnet.

18. The method of claim 16, wherein the prosthetic linking structure includes one or more of a fibrous, filamentous, organic polymer, woven, braid, and fabric material.

19. The method of claim 18, wherein the prosthetic linking structure includes a fabric sleeve enclosing a solid resilient polymer positioned between the first end portion and the second end portion, the first end portion defines a first magnetic pole and the second end portion defines a second magnetic pole, the first end portion and the second end portion are oriented to direct the first magnetic pole and the second magnetic pole towards one another, the first magnetic pole and the second magnetic pole being of the same type to provide the repulsive magnetic force.

20. The method of claim 16, wherein the selectively adjusting of the at least one of the first and second magnetic fields occurs when the spinal disk prosthesis is implanted between the first vertebra and the second vertebra with the spinal disk prosthesis maintained in the cavity between the first and second vertebrae to adjust the repulsive magnetic force between the first and second portions to the desired load bearing level.

* * * * *